United States Patent [19]

DeLuca

[11] 4,096,862

[45] Jun. 27, 1978

[54] LOCATING OF TUBES IN THE HUMAN BODY

[76] Inventor: Salvatore A. DeLuca, 607 Revere Beach Blvd., Revere, Mass. 02151

[21] Appl. No.: 687,103

[22] Filed: May 17, 1976

[51] Int. Cl.$^2$ ............................................. A61M 25/00
[52] U.S. Cl. .................................. 128/348; 128/1.2; 128/2.05 D; 350/303
[58] Field of Search ........ 128/2 A, 1.1, 2 M, DIG. 9, 128/1.2, 348, 2.05 D, 2 P; 250/303

[56] References Cited

U.S. PATENT DOCUMENTS

| 1,867,624 | 7/1932  | Hoffman ........................... 128/1.2 X |
| 3,093,739 | 6/1963  | Danforth et al. ..................... 250/303 |
| 3,399,668 | 9/1968  | Lundgren ............................. 128/2 A |
| 3,750,653 | 8/1973  | Simon .................................. 128/1.2 |
| 3,847,157 | 11/1974 | Caillouette et al. .................. 128/348 |

FOREIGN PATENT DOCUMENTS 857,992   1/1961   United Kingdom ................... 128/1.2

OTHER PUBLICATIONS

"Magnetic Intubation," by H. Frank McCarthy, M.D. et al.
*The Evening Star* Washington, D.C., pp. A-20, 7-1964, "Radio Tags Bar Sponges in Patients".

*Primary Examiner*—Robert W. Michell
*Assistant Examiner*—Michael H. Thaler
*Attorney, Agent, or Firm*—Clarence A. O'Brien; Harvey B. Jacobson

[57] ABSTRACT

A method for locating tubes, or internal lines, disposed within a passage of a body of a patient by means of radionuclides. A radioactive element is inserted into a line, such as a catheter, disposed in a body passage and is detected by a radiation measuring instrument, such as a Geiger counter, in order to locate the line. By monitoring the radioactive element as it is being inserted into the line, the entire course of the line within the patient's body can be accurately determined.

2 Claims, 7 Drawing Figures

U.S. Patent  June 27, 1978  4,096,862
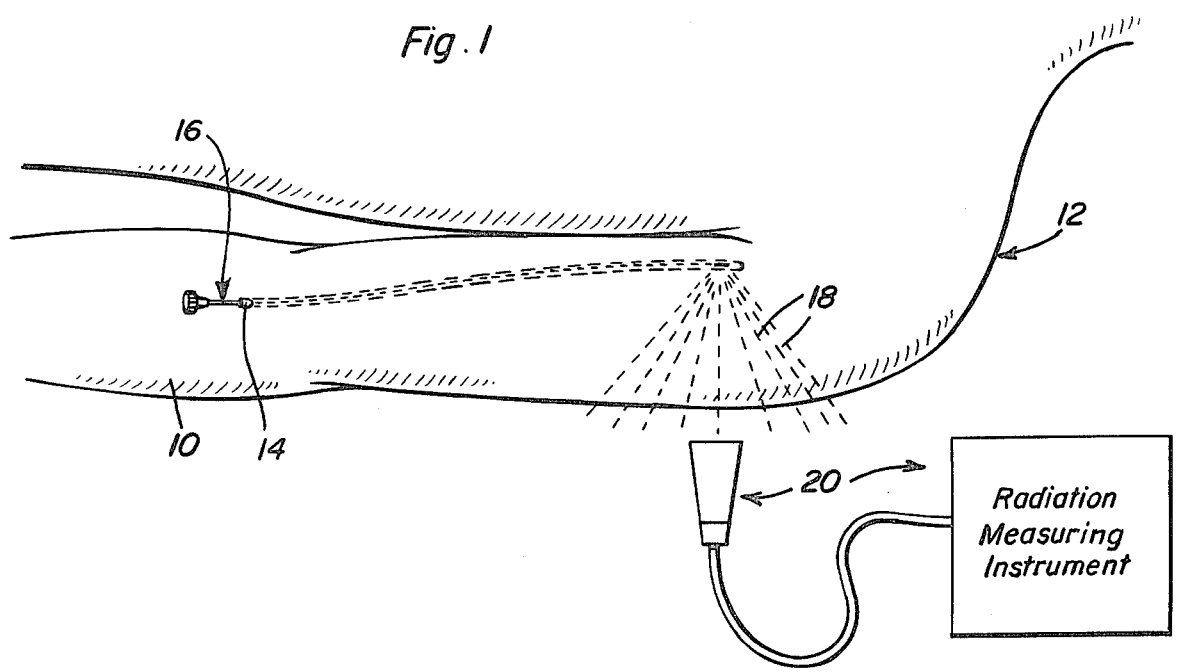
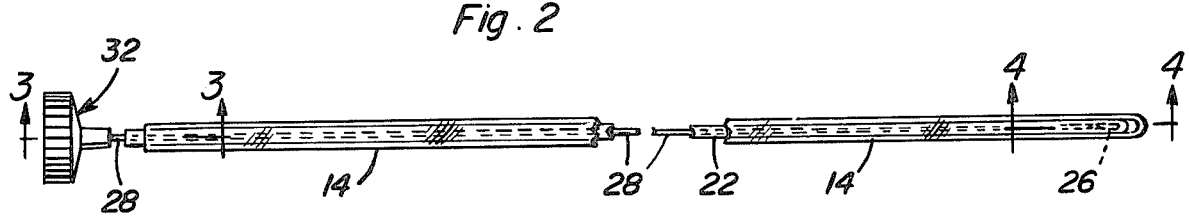
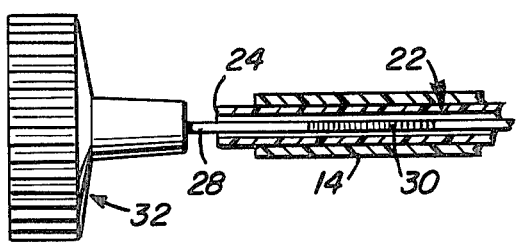
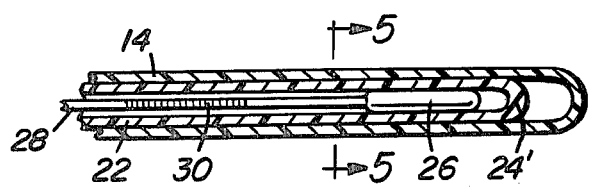
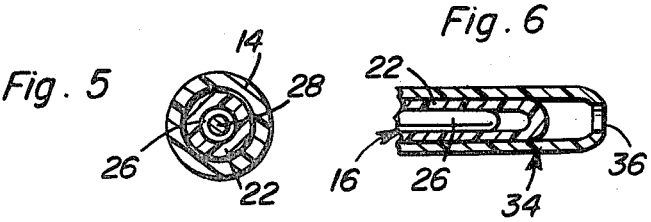
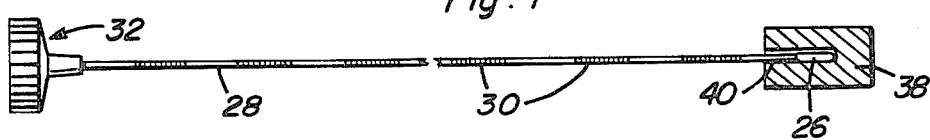

LOCATING OF TUBES IN THE HUMAN BODY

BACKGROUND OF THE INVENTION

1. Field of the Invention

This invention relates generally to the use of the catheters and similar tubes within the human body, and particularly to the determination of the location of such tubes within the patient.

2. Description of the Prior Art

Central venous pressure (CVP) lines are used extensively in hospital intensive care units (ICU's) to monitor blood pressure. They also serve as a pathway for the injection of intravenous solutions. These pressure lines are hollow wires or tubes that are inserted and fed into a patient's vein in order to measure and monitor the pressure of the blood emanating from certain sections of the body. In order to obtain accurate readings, it is essential to locate the exact position of the tube in the human body, since normal pressure varies at different locations in the body.

At the present, the only method of visualizing the tube, or line, in the body is by the use of X-ray; however, this entails the use of a portable X-ray unit, which is expensive, inconvenient, time-consuming, and not always readily available. In addition, and of major significance, is the source of X-ray radiation to the patient and personnel in the ICU units. Oftentimes multiple X-rays are necessary if the first X-ray report indicates that the line is not in its proper place, since correction of position will, also, be monitored by X-ray.

It is known generally to employ radionuclides in the diagnosis and treatment of various diseases. Examples of methods and devices which employ radioactive materials are found in U.S. Pat. Nos. 3,719,183, issued Mar. 6, 1973 to H. S. Schwartz; 3,741,198, issued June 26, 1973 to C. Burton; and 3,866,050, issued Feb. 11, 1975 to D. Whitfield.

SUMMARY OF THE INVENTION

It is an object of the present invention to provide a simple, accurate, and inexpensive method of locating the position of catheters, and the like.

It is another object of the present invention to provide a system which permits catheters and similar lines inserted in a patient's body to be simply, accurately, and inexpensively located.

These and other objects are achieved according to the present invention by providing a method for locating internal lines which has the steps of: inserting a line into a passage in a patient's body; inserting a radioactive source into the line inserted in the patient's body; and monitoring with a radiation measuring instrument the radioactive source inserted into the patient's body and determining the location of the line at a given position of the radioactive source.

The radioactive source advantageously includes a radioactive element disposed within a sheath closed at the end adjacent the radioactive source. Further, an elongated element, such as a length of wire, is connected to the radioactive source and arranged extending out of the sheath for connection to a handle facilitating manipulation of the radioactive element both when the radioactive element is being inserted into a catheter, and the like, and at times when the radioactive element is not being used and is suitably stored.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a fragmentary, schematic representation showing how the position of a line, such as a catheter, within a patient's body is located in accordance with the present invention.

FIG. 2 is a fragmentary, side elevational view showing line locating apparatus according to the present invention.

FIG. 3 is a fragmentary, enlarged, sectional view taken generally along the line 3—3 of FIG. 2.

FIG. 4 is a fragmentary, enlarged, sectional view taken generally along the line 4—4 of FIG. 2.

FIG. 5 is an enlarged, sectional view taken generally along the line 5—5 of FIG. 4.

FIG. 6 is a fragmentary, sectional view similar to FIG. 4, but showing a modified form of the invention.

FIG. 7 is a fragmentary, side elevational view, partly in section, showing a manner of storing a radioactive element used in carrying out the invention when the radioactive element is not being used.

DESCRIPTION OF THE PREFERRED EMBODIMENTS

Referring now more particularly to FIG. 1 of the drawings, an arm 10 of a patient 12 has inserted in, for example, a vein thereof a conventional catheter 14, and the like, such as those catheters referred to as central venous tubes. A radioactive souce assembly 16 according to the present invention is illustrated as inserted in the catheter 14, while radiation 18 emanating from the radiation source assembly 16 is being monitored by a radiation measuring instrument 20. The latter may be any conventional radiation measuring instrument or counter, such as the well known Geiger counter.

Referring now more particularly to FIGS. 2 through 5 of the drawing, assembly 16 includes a sheath 22, which may be a conventional disposable catheter constructed from a suitable material such as polytetrafluoroethylene, and has a pair of spaced ends 24 and 24', with end 24 being open and end 24' being closed. A radioactive element 26 is disposed adjacent the closed end 24' of sheath 22 in order to protect the element 26 from contamination by the body fluids, and the like, flowing through catheter 14.

Assembly 16 further includes, in addition to sheath 22 which is arrangeable coaxially within catheter 14, and the radioactive element 26, an elongated element 28, which may be a length of wire, on which element 26 is mounted and which extends axially through sheath 22 and out open end 24. This element 28 is provided with appropriate indicia 30 for calibrating the length of element 28 in, for example, centimeters, while a handle 32 is attached to the outer end of element 28 in a conventional manner for facilitating manipulation of element 28 and, accordingly, radioactive element 26. More specifically, element 26 forms the inward tip of element 28, and can be constructed in any suitable, known manner, such as by the use of a solidifying liquid, a screw-on piece of radioactive material, or a welded piece of radioactive material. Ideally, the tip, or element 26, will be of the same cross-sectional dimension and circumference as element 28.

While the nose, or right-hand end, of catheter 14 is illustrated in FIGS. 2 through 5 as being a closed end, it is possible, and necessary in some instances, to have both ends of the catheter 14, and the like, open. Accordingly, FIG. 6 shows a catheter 34 similar to catheter 14, but having an open end 36 at the end of the catheter 34 disposed adjacent the radioactive element 26 of assembly 16.

FIG. 7 of the drawing shows a possible manner of storing the assembly 16, absent the disposable sheath 22, when the assembly 16 is not being used. More specifically, a lead block 38, and the like, is provided with a recess 40 which receives the radioactive element 26 for shielding element 26 and preventing possibly harmful rays from contaminating substances, including human tissue, which may be adjacent to radioactive element 26.

In summary, therefore, the present invention involves the use of a standard CVP tube or line, or an endotracheal tube, a chest tube, and the like, together with an additional line of a smaller diameter, which may be a conventional disposable catheter, inserted and fed into the standard line. The end of the smaller catheter is closed or sealed off. A wire, and the like, is then inserted into the smaller diameter catheter, with the tip of the wire fed into the sealed portion of the smaller diameter catheter being radioactive. Exposure to radiation will be negligibel, since it is of low intensity and significantly lower than the radiation emitted from X-ray machines. The radioactive tip will be accurately detected externally by an inexpensive hand-held Geiger counter, and the like, commercially available.

The elongated elements 28 with the radioactive element 26 forming a tip thereof and provided with handle 32 can be used repeatedly on different patients since patient contact and germ contact is eliminated by use of the sealed sheath 22 which prevents contact with body fluids of the patients.

The sealed sheath 22 which acts as a glove for the radioactive element 26 is usually thrown away after each use, with the radioactive element 26, together with the associated elongated element 28 and handle 32, being stored in lead, and the like, for subsequent testing as described above with regards to FIG. 7. An advantageous feature of the invention is that the Geiger counter, and the like, can be used while the radioactive element 26 is being inserted into the catheter 14 for determining the direction of the catheter 14 at any particular point and to eliminate any errors in the original placement of the catheter 14.

A typical kit for carrying out the present invention can include a Geiger counter, elongated element 28 supporting radioactive element 26, a series of disposable catheters forming sheath 22, and a series of disposable catheters 14.

Not only is the equipment used to carry out the present invention relatively inexpensive, but the present invention eliminates in addition to the use of X-ray machines the need for interpretation of X-ray photographs, and the like.

Furthermore, statistics have demonstrated that between one-third and one-half of all X-rays taken in intensive care units are for the purpose of locating CVP lines. This inconvenience, expense, and potential hazard is eliminated by the present invention.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A method for locating internal lines within a passage of a patient's body, comprising the steps of:
    (a) inserting a line into a passage of a patient;
    (b) inserting a finite radioactive source into the line inserted by step (a), the inserting step (b) including the step of placing a single discrete radioactive element inside a sheath closed only at one end for preventing contamination of the radioactive element; and
    (c) monitoring with a radiation measuring instrument the radioactive source inserted by step (b) and determining the location of the line at the position of the radioactive source.

2. A method as set forth in claim 1, wherein the inserting step (b) includes the step of measuring the length the radioactive element is inserted into the line.

* * * * *